United States Patent [19]  [11]  4,347,233
Yamauchi et al.  [45]  Aug. 31, 1982

[54] DENTAL CARIES DETECTION

[75] Inventors: Junichi Yamauchi; Kyoichiro Shibatani; Eiji Ikeguchi; Ikuo Omura; Yoshinori Nagase, all of Kurashiki, Japan

[73] Assignee: Kuraray Company, Limited, Kurashiki, Japan

[21] Appl. No.: 98,686

[22] Filed: Nov. 29, 1979

[30] Foreign Application Priority Data

Dec. 4, 1978 [JP] Japan .................. 53-150410

[51] Int. Cl.³ .............. A61K 6/00; A61K 49/00; G01N 1/30; G01N 21/25
[52] U.S. Cl. ............................. 424/7; 424/9; 424/49
[58] Field of Search .................. 424/7, 9, 49

[56] References Cited

U.S. PATENT DOCUMENTS

| 3,279,068 | 10/1966 | Stark | 424/9 X |
|---|---|---|---|
| 3,309,274 | 3/1967 | Brilliant | 424/7 |
| 3,723,613 | 3/1973 | Block | 424/49 X |
| 4,204,978 | 5/1980 | Ibsen | 424/7 X |

FOREIGN PATENT DOCUMENTS

| 2347037 | 11/1977 | France | 424/7 |
|---|---|---|---|
| 51-38427 | 3/1976 | Japan | 424/7 |
| 51-38428 | 3/1976 | Japan | 424/7 |
| 51-38429 | 3/1976 | Japan | 424/7 |
| 1560757 | 2/1980 | United Kingdom | 424/7 |

OTHER PUBLICATIONS

Fusayama (3), Operative Dent., vol. 4, 1979, pp. 63–70.
Lang, J. Periodont. Res., vol. 7, 1976, pp. 59–67.
Lazzari, Dent. Biochem., Lea Febiger, Philadelphia, 2nd Ed., 1976, pp. 4–7, 15–39.
Newbrun, Cariology, Williams & Wilkins, Baltimore, pp. 162–167, 200–207.
Lange, Dtsch. Zahnarztl. Z., vol. 29, 1974, pp. 13–18.
Lange, Quintessenz. Journal, vol. 6, 1974, pp. 35–38.
Christen, Chem. Abs., vol. 66, 1967, p. 7880, Ab. No. 84289z.
Bouquet, Rev. Franc. d'Odonto-Strom., vol. 18, Dec. 1971, pp. 1239–1251, 1260–1261.
Kieser, J. of Clinical Periodontology, vol. 3, 1976, pp. 200–207.
Balsam, Cosmetics, Sci. & Tech., Wiley-Intersci., N.Y., 2nd Ed., vol. 1, 1972, pp. 428–436, 490–500, 547, 548, 550–552; vol. 3, 1974, pp. 548–550, 556–557.
H. J. Conn's Biological Stains, Williams & Wilkins, Baltimore, 9th Ed., 1977, pp. 330–337.

Primary Examiner—Anna P. Fagelson
Attorney, Agent, or Firm—Oblon, Fisher, Spivak, McClelland & Maier

[57] ABSTRACT

A caries detector, comprising a solution of a dye selected from the group consisting of Phloxine B (CI 45410), Phloxine BK (the corresponding dipotassium salt of CI 45410), Acid Red (CI 45100), Fast Acid Magenta (CI 17200), Fast Green FCF (CI 42053) and Rhodamine B (CI 45170) in a solvent.

3 Claims, No Drawings

DENTAL CARIES DETECTION

BACKGROUND OF THE INVENTION

1. Field of the Invention

The present invention relates to a caries detector for the selective dyeing of dental caries which enables the same to be accurately detected in the treatment of decayed teeth.

2. Description of the Prior Art

In the treatment of diseased teeth, it is necessary to completely eliminate the carious portions from the teeth. On the other hand, it is undesirable to cut and eliminate the sound portions of the teeth at the same time. Heretofore, the carious portion of a decayed tooth has been differentiated from the sound portion of the tooth by virtue of the difference in hardness between sound and decayed portions or by the difference in color between sound and decayed portions which results from the spontaneous discoloration of the carious portion of the tooth. These differences, however, do not show a clearly detectable boundary between sound and decayed areas, and in the final judgement, the dentist must rely upon his experience to discern the boundaries of the decayed portions of a tooth. Thus, excessive cutting has generally been practiced because excessive cutting which extends even to the sound dental portion is preferred to the leaving of an uncut area in the carious portion. Recently, however, dental practitioners are increasingly believing that it is important to preserve the sound dental portions of a tooth as much as possible, thus minimizing the sacrificing of decayed teeth, and to avoid exposure of the dental pulp by cutting and eliminating the portions of the tooth near the dental pulp. A need therefore, exists for a detecting reagent which accurately detects only the carious portion of a tooth which is to be eliminated. Reagents containing basic fuchsin are already known as detecting reagents (Japanese Laid-Open Patent Publication No. 38428/1976). However, the known reagents are undesirable because of their suspected safety.

SUMMARY OF THE INVENTION

Accordingly, one object of the present invention to provide a caries detector which enables dental caries to be accurately detected in the treatment of decayed teeth and which has a high level of safety.

Another object of the present invention is to provide a caries detector which has the function of differentiating between the sound portion and the carious portion of a tooth by its ability to selectively dye the carious portion of the tooth.

Briefly, these objects and other objects of the present invention as hereinafter will become more readily apparent can be obtained by a caries detector composed of a solution of a dye selected from the group consisting of Phloxine B (CI 45410), Phloxine BK (the corresponding dipotassium salt of CI 45410), Acid Red (CI 45100), Fast Acid Magenta (CI 17200), Fast Green FCF (CI 42053) and Rhodamine B (CI 45170).

DETAILED DESCRIPTION OF THE PREFERRED EMBODIMENTS

By chemical nomenclature, the dyes employed in the formulation of the caries detector of the present invention are as follows:

(1) Phloxine B (CI 45410) (Generic name, CI Acid Red 92)
Disodium salt of 9-(3,4,5,6-tetrachloro-ortho-carboxy-phenyl)-6-hydroxy-2,4,5,7-tetrabromo-3-isoxanthone.

(2) Phloxine BK (the corresponding dipotassium salt of CI 45410)
Dipotassium salt of 9-(3,4,5,6-tetrachloro-ortho-carboxyphenyl)-6-hydroxy-2,4,5,7-tetrabromo-3-isoxanthone.

(3) Acid Red (CI 45100) (CI Acid Red 52)
Monosodium salt of 9-(4-sulfo-2-sulfoniumphenyl)-6-diethylamino-3-(N,N-diethylimino)-3-isoxanthene.

(4) Fast Acid Magenta (CI 17200) (CI Acid Red 33)
Disodium salt of 8-amino-2-phenylazo-1-naphthol-3,6-disulfonic acid.

(5) Fast Green FCF (CI 42053) (CI Food Green 3)
Disodium salt of 4-{[4-(N-ethyl-meta-sulfobenzylamino)-phenyl]-(4-hydroxy-2-sulfoniumphenyl)-methylene}-[1-(N-ethyl-N-meta-sulfobenzyl)$\Delta^{2,5}$-cyclohexadienimine].

(6) Rhodamine B (CI 45170) (CI Basic Violet 10)
3-Ethochloride of 9-ortho-carboxyphenyl-6-diethylamino-3-ethylimino-3-isoxanthene.

The caries detector of this invention is prepared by dissolving at least one of the above dyes in a solvent.

The concentration of the dye in the solution is preferably 0.1 to 5% by weight. If the concentration is less than 0.1% by weight, the resulting caries detector does not permit sufficient coloration of a dental caries. If the concentration is greater than 5% by weight, the coloration of the detector extends even to the sound dental portion, thereby rendering it difficult to detect solely the carious portion of the tooth. Preferably, the concentration of the dye in the solution is 1 to 2% by weight.

By the use of the specified dyes, the caries detector of the present invention can clearly color only the carious portion of a tooth, and therefore, the carious portion can be clearly differentiated from the sound portion. Rhodamine B and Acid Red are especially preferred dyes. These particular dyes are officially approved in Japan as highly safe dyes for foodstuffs and for medicines that can be applied to the mucous membrane. The dyes used in the present invention are abbreviated in Japan as follows:

| Phloxine B | Red No. 104 |
| Phloxine BK | Red No. 231 |
| Acid Red | Red No. 106 |
| Fast Acid Magenta | Red No. 227 |
| Fast Green FCF | Green No. 3 |
| Rhodamine B | Red 213 |

The dyes used in the present invention can be easily obtained because they are commercially available. It is known that Fast Acid Magenta can be used as an agent for revealing dental plaque (West German Laid-Open Patent Publication (OLS) No. 2715521). The German specification, however, does not disclose that this dye colors dental caries.

Any solvent which dissolves the above mentioned dyes and is not hazardous to humans may be used in the caries detector of the present invention. Examples include water, alcohols, tetrahydrofuran, dimethylformamide, dioxane, acetone and dimethoxyethane. Organic mono-, di- or tri-hydroxy compounds containing 1, 2 or 3 hydroxy groups per molecule and from 2 to 10 carbon atoms per molecule are preferred because they serve to enhance the penetrability of the dye into the carious portion and permit clear dyeing of the carious portion. Compounds containing four or more hydroxyl groups per molecule are not practical because they have a high viscosity, and compounds having 11 or more carbon atoms are undesirable because the solubility of the dyes in these compounds is low.

Usually aliphatic hydroxy compounds are employed as the solvent medium for the detector of the present invention. Examples of suitable monohydroxy compounds include monohydric alcohols such as ethanol, n-propanol, isopropanol, isobutyl alcohol, n-amyl alcohol, isoamyl alcohol, neopentyl alcohol, 2-hexanol, 1-heptanol, nonyl alcohol and decyl alcohol; monoethers of dihydric alcohols such as ethylene glycol monomethyl ether, ethylene glycol monoethyl ether, ethyleneglycol monobutyl ether, diethylene glycol monoethyl ether, diethylene glycol monobutyl ether, triethylene glycol monomethyl ether, triethylene glycol monoethyl ether, tetraethylene glycol monomethyl ether and tetraethylene glycol monoethyl ether; monoesters of dihydric alcohols such as ethylene glycol monoacetate and diethylene glycol monoacetate. Examples of suitable dihydroxy compounds include dihydric alcohols such as ethylene glycol, propylene glycol, 1,3-propanediol, 1,2-butanediol, 1,4-butanediol, diethylene glycol, triethylene glycol, tetraethylene glycol, pentaethylene glycol and dipropylene glycol, and monoethers and monoesters of trihydric alcohols such as glycerin monomethyl ether and glycerin monoacetate. Examples of suitable trihydroxy compounds include glycerol and pentaglycerol. Of these, triethylene glycol and propylene glycol are preferred. The hydroxy compounds can be used either alone or in a combination of two or more.

Preferred detectors of the present invention are obtained by dissolving the indicated dyes in the above mentioned hydroxy compounds, or mixtures of these hydroxy compounds with other solvents such as water. Because it is advantageous in the dyeing of dental caries, that the dye penetrate rapidly into the dental caries which has a less dense structure than the sound dental portion, the solvent for the caries detector preferably comprises at least 60% by weight, preferably at least 80% by weight of each of the above hydroxy compounds which have high penetrability. If water is mixed in a higher proportion, the rate of penetration of the dye decreases so that the selectivity of dyeing of the dental caries, which depends in part upon the difference in the rate of penetration between the carious portion and the sound portion, tends to be reduced. Usually, the solvent is composed substantially of a hydroxy compound.

The caries detector of the present invention is prepared, for example, by adding the required amount of the dye to the solvent, and stirring the mixture at room temperature or an elevated temperature. Alternatively, the dye can be dissolved in the solvent in an amount larger than the required amount, and then prior to use, the solution is diluted to provide a caries detector having the desired dye concentration. The caries detector of this invention is stable during storage over extended periods of time.

In applying the caries detector of the present invention to the dental caries of a patient, the detector is put into a receptacle with an elongated nozzle, and a small amount, i.e. about 1 to several drops, of it is added to the carious portion. The amount of the detector solution needed is small, normally about 0.02 to 0.2 cc (The amount of the dye applied ranges from 0.00002 to 0.005 gr). The dental caries is first dyed, and with time, the sound portion of the tooth becomes slightly colored, Hence, in 1 to 10 seconds after application of the detector to the tooth, the remaining solution should be washed away. Washing is effected by spraying a suitable amount of water to the tooth, and exhausting it by vacuum ejector. By this operation, the carious portion is vividly dyed, while the sound dentin is barely stained, thus providing accurate detection of the carious portion of a tooth. Since the dentist can accurately locate a portion of a tooth to be eliminated in the treatment of decayed teeth by using the detector of the present invention, the detector is very effective in treatment of decayed teeth. The caries detector of the invention also permits selective coloration of dental caries at the early stage of development where no spontaneous discoloration occurs. Hence, the presence of dental caries in early stages of development can be determined.

Having generally described this invention, a further understanding can be obtained by reference to certain specific examples which are provided herein for purpose of illustration only and are not intended to be limiting unless otherwise specified.

EXAMPLES 1 TO 10 AND COMPARATIVE EXAMPLES 1 TO 3

The various detecting reagents shown in Table 1 were prepared by mixing the various dyes and organic solvents shown in Table 1 at room temperature with stirring. The ability of each of these reagents to differentiate the carious portion of a tooth by dyeing was examined using the cut surface of an extracted decayed tooth as a sample. Several drops of the reagent were applied to the cut surface of the decayed tooth, and in about 5 seconds, the applied portion was washed with water and observed. In this way, it could be determined whether the carious portion and the sound dentin portion originally distinguishable by the differences in color and hardness could be more clearly differentiated by dyeing. The results are shown in Table 1. For comparative purposes, the results obtained with other dyes are also given in Table 1.

The differentiating ability by dyeing was evaluated on the following scale.

++: dyed vividly
+: dyed
+−: slightly dyed
−: barely dyed

TABLE 1

| Example (Ex.) or Comparative Example (CEx.) | Dye | Solvent | Concentration of the dye (wt. %) | Degree of dye fixation | |
|---|---|---|---|---|---|
| | | | | Carious portion | Sound portion |
| Ex. 1 | Phloxine BK | Propylene glycol | 1.0 | + | − |
| Ex. 2 | Acid Red | Propylene glycol | " | ++ | − |
| Ex. 3 | Fast Acid Magenta | Propylene glycol | " | + | − |
| Ex. 4 | Phloxine B | Propylene glycol | " | + | − |
| Ex. 5 | Fast Green FCF | Propylene | " | + | − |

TABLE 1-continued

| Example (Ex.) or Comparative Example (CEx.) | Dye | Solvent | Concentration of the dye (wt. %) | Degree of dye fixation Carious portion | Degree of dye fixation Sound portion |
|---|---|---|---|---|---|
| Ex. 6 | Rhodamine B | Propylene glycol | " | ++ | — |
| Ex. 7 | " | Triethylene glycol | " | ++ | — |
| Ex. 8 | " | Triethylene glycol | 2.0 | ++ | — |
| Ex. 9 | Acid Red | Triethylene glycol | 1.0 | ++ | — |
| Ex. 10 | " | Triethylene glycol | 2.0 | ++ | — |
| CEx. 1 | New Coccine | Propylene glycol | 1.0 | +— | — |
| CEx. 2 | Eosine YS | Propylene glycol | " | +— | — |
| CEx. 3 | Light Green SF | Propylene glycol | " | +— | — |

As can be discerned from the above results, the detecting reagents of the present invention can clearly differentiate the carious portion from the sound dentin portion in a tooth. Particularly, the detectors shown in Examples 2, 6, 7, 8, 9 and 10 obtained by using Rhodamine B and Acid Red as dyes and triethylene glycol and propylene glycol as solvents vividly dye the carious portions of teeth, and permit easier differentiation of the carious portions from the sound dentin portions.

As can be discerned from the Comparative Examples, when acid or basic dyes of the same series as the dyes used in this invention are used, the carious portion is dyed only slightly. This evidence shows that the dyes used in the present invention are very effective.

EXAMPLE 11

Acid Red was dissolved in each of the solvents shown in Table 2 to a concentration of 1% by weight to prepare detecting reagents. The ability of each of these reagents to differentiate dental caries by dyeing was examined in the same way as in Examples 1 to 10. The results are shown in Table 2.

TABLE 2

| Solvent | Degree of dye fixation carious portion | Degree of dye fixation sound dentin |
|---|---|---|
| Triethylene glycol | ++ | — |
| Triethylene glycol/water (80/20 by weight percent) | ++ | — |
| Triethylene glycol/water (50/50 by weight percent) | ++ | — to +— |

As is evident from Table 2, the detector formulated from a solvent system consisting of 80% by weight of triethylene glycol and 20% by weight of water showed excellent differentiating ability, but when the water content of the solvent was 50% by weight, the resulting detector showed a somewhat decreased dying ability.

EXAMPLE 12

Detecting reagents were prepared by dissolving Acid Red in each of the solvents shown in Table 3. The ability of each of the reagents to differentiate dental caries by dyeing was examined in the same way as in Examples 1 to 10. The results are shown in Table 3.

TABLE 3

| Dye concentration (wt. %) | Solvent | Degree of dye fixation Carious portion | Degree of dye fixation Sound dentin |
|---|---|---|---|
| 0.5 | n-Propanol | + | — |
| 1.0 | Ethylene glycol monoacetate | ++ | — |
| 1.0 | Glycerol | ++ | — |

It is evident from Table 3 that detecting reagents obtained by using n-propanol, ethylene glycol monoacetate and glycerol as solvents showed excellent differentiating ability.

EXAMPLE 13

One gram of Acid Red was added to 100 g of triethylene glycol, and the mixture was stirred at room temperature to prepare a 1% triethylene glycol solution of Acid Red. Using the resulting solution as a caries detector, a clinical test was conducted.

Using a turbine fitted with a spherical carbide bar, the decayed free enamel was completely eliminated from the first molar having a carious portion, and the carious portion was extended. Then, the heavily colored carious dentin was almost completely removed by using an electric engine or spoon excavator fitted with a spherical steel bar. One drop of the above caries detector was applied to the cavity. Several seconds later, it was washed away with a water jet. A portion which was dyed deep red remained. This portion was again cut off by using the electric engine or spoon excavator. Then, again, one drop of the above detecting reagent was applied to the cavity, and the state of dye fixation was observed. A small portion which was dyed red still remained. When the above operation was repeated twice, no portion was observed which was dyed by applying drops of the reagent. The remaining dentin was determined to be a normal sound dentin portion that should be retained for the restoration of the tooth.

From the above examples, it is evident that the caries detector of this invention can be effectively utilized for the treatment of decayed teeth.

Having now fully described this invention, it will be apparent to one of ordinary skill in the art that many changes and modifications can be made thereto without departing from the spirit or scope of the invention as set forth herein.

What is claimed:

1. A method for distinguishing, by observation with visible light, between the carious portion and the sound portion of a decaying tooth by selectively dyeing the carious portion, which comprises applying a solution of Acid Red (CI 45100) in a concentration of from 0.1 to 5.0% by weight in a solvent which comprises at least 60% by weight of a mono-, di- or tri-hydroxy compound containing 2 to 20 carbon atoms to a decayed tooth to selectively dye the carious portion of the tooth, and then within 10 seconds after applying the solution washing away the remaining solution before the sound portion of the tooth is dyed with said solution.

2. The method of claim 1, wherein said solvent comprises at least 80% by weight of the mono-, di- or tri-hydroxy compound containing 2 to 10 carbon atoms.

3. The method of claim 2, wherein said solvent is triethylene glycol or propylene glycol.

* * * * *